(12) United States Patent
Wallace

(10) Patent No.: US 12,350,183 B2
(45) Date of Patent: Jul. 8, 2025

(54) ADJUSTABLE NASAL DILATOR

(71) Applicant: Nasal Dilator LLC, Hartford, CT (US)

(72) Inventor: Tom Wallace, Durham, CT (US)

(73) Assignee: NASAL DILATOR LLC, Hartford, CT (US)

( * ) Notice: Subject to any disclaimer, the term of this patent is extended or adjusted under 35 U.S.C. 154(b) by 407 days.

(21) Appl. No.: 18/075,113

(22) Filed: Dec. 5, 2022

(65) Prior Publication Data

US 2023/0114880 A1 Apr. 13, 2023

Related U.S. Application Data

(63) Continuation-in-part of application No. 16/855,545, filed on Apr. 22, 2020, now Pat. No. 11,672,688.

(60) Provisional application No. 62/837,465, filed on Apr. 23, 2019.

(51) Int. Cl.
*A61F 5/08* (2006.01)
(52) U.S. Cl.
CPC ...................................... *A61F 5/08* (2013.01)
(58) Field of Classification Search
CPC ....... A61F 5/08; A61M 15/08; A61M 15/085; A61M 15/002; A61M 2210/0618
See application file for complete search history.

(56) References Cited

U.S. PATENT DOCUMENTS

| | | | |
|---|---|---|---|
| 5,816,241 A | 10/1998 | Cook | |
| 5,989,270 A | 11/1999 | Suh et al. | |
| 6,238,411 B1 | 5/2001 | Thorner | |
| 6,863,066 B2 | 3/2005 | Ogle | |
| 7,105,008 B2 | 9/2006 | Maryanka | |
| 8,834,512 B1 | 9/2014 | Brown et al. | |
| 2006/0260613 A1* | 11/2006 | Pinter | A61M 15/08 128/206.11 |
| 2010/0063532 A1 | 3/2010 | Moore | |
| 2013/0157810 A1 | 6/2013 | McDevitt et al. | |
| 2015/0173934 A1 | 6/2015 | Castillo | |
| 2020/0337877 A1 | 10/2020 | Wallace | |

\* cited by examiner

*Primary Examiner* — Majid Jamialahmadi
(74) *Attorney, Agent, or Firm* — CANTOR COLBURN LLP

(57) ABSTRACT

A nasal dilator includes a first leg and a second leg. The second leg is movable relative to the first leg between a first position and a second position. The second leg is arranged at an angle relative to the first leg in both the first position and the second position. A first support member extends from the first leg such that a first clearance configured to receive a first nostril ala is formed between the first leg and the first support member. A second support member extends from the second leg such that a second clearance configured to receive a second nostril ala is formed between the second leg and the second support member. An adjustment mechanism is operable to move the second leg between the first position and the second position.

16 Claims, 4 Drawing Sheets

ADJUSTABLE NASAL DILATOR

CROSS-REFERENCE TO RELATED APPLICATIONS

This application is a continuation-in-part which claims priority to U.S. Non-Provisional application Ser. No. 16/855,545, filed on Apr. 22, 2020, which claims priority to U.S. Provisional Application No. 62/837,465, which was filed on Apr. 23, 2019, the contents of both of which are incorporated herein by reference.

BACKGROUND

Every year millions of individuals spray chemicals into their nostrils and attach devices to their noses in an attempt to improve nasal breathing. A large percentage of the human population experiences periodic nasal air passage restrictions resulting from sinus irritations, changes in barometric pressure, nasal structure and other causes. This condition is particularly bothersome at night and often causes poor air filtration, disrupted sleep patterns, excessive breathing through the mouth, dry mouth, snoring, and other discomforts and health problems.

SUMMARY

According to an embodiment, a nasal dilator includes a first leg and a second leg. The second leg is movable relative to the first leg between a first position and a second position. The second leg is arranged at an angle relative to the first leg in both the first position and the second position. A first support member extends from the first leg such that a first clearance configured to receive a first nostril ala is formed between the first leg and the first support member. A second support member extends from the second leg such that a second clearance configured to receive a second nostril ala is formed between the second leg and the second support member. An adjustment mechanism is operable to move the second leg between the first position and the second position.

In addition to one or more of the features described above, or as an alternative, in further embodiments the first support member is integrally formed with the first leg and the second support member is integrally formed with the second leg.

In addition to one or more of the features described above, or as an alternative, in further embodiments a distal end of the first support member and the second support member extends beyond the distal end of the first leg and the second leg, respectively.

In addition to one or more of the features described above, or as an alternative, in further embodiments a distal end of the first support member and the second support member extends is aligned with the distal end of the first leg and the second leg, respectively.

In addition to one or more of the features described above, or as an alternative, in further embodiments including a connecting member coupling the first leg and the second leg.

In addition to one or more of the features described above, or as an alternative, in further embodiments the first leg, the second leg, and the connecting member are integrally formed.

In addition to one or more of the features described above, or as an alternative, in further embodiments a first contact region is formed at an exterior surface of the first leg and a second contact region is formed at the exterior surface of the second leg.

In addition to one or more of the features described above, or as an alternative, in further embodiments at least one of the first contact region and the second contact region includes a contoured surface for gripping a nasal surface.

In addition to one or more of the features described above, or as an alternative, in further embodiments each of the first contact region and the second contact region is formed by a pad mounted to a distal end of the first leg and the second leg, respectively.

In addition to one or more of the features described above, or as an alternative, in further embodiments a first external contact region is formed at an interior surface of the first support member and a second external contact region is formed at the interior surface of the second support member.

In addition to one or more of the features described above, or as an alternative, in further embodiments the first contact region is aligned with the first external contact region and the second contact region is aligned with the second external contact region.

In addition to one or more of the features described above, or as an alternative, in further embodiments the first support member and the second support member have a curved configuration such that the first clearance varies over a length of the first leg and the second clearance varies over the length of the second leg.

In addition to one or more of the features described above, or as an alternative, in further embodiments the first clearance is smallest between the first contact region and the first external contact region and the second clearance is smallest between the second contact region and the second external contact region.

In addition to one or more of the features described above, or as an alternative, in further embodiments the first support member and the second support member are formed from a resilient material.

In addition to one or more of the features described above, or as an alternative, in further embodiments the adjustment mechanism includes a tension control rod rotatable about an axis to vary a position of the second leg.

In addition to one or more of the features described above, or as an alternative, in further embodiments lateral movement of the tension control rod is restricted relative to at least one of the first leg and the second leg.

In addition to one or more of the features described above, or as an alternative, in further embodiments the tension control rod is threadably coupled to at least one of the first leg and the second leg.

BRIEF DESCRIPTION OF THE FIGURES

The accompanying drawings incorporated in and forming a part of the specification embodies several aspects of the present disclosure and, together with the description, serves to explain the principles of the disclosure. In the drawings.

Figure 1:
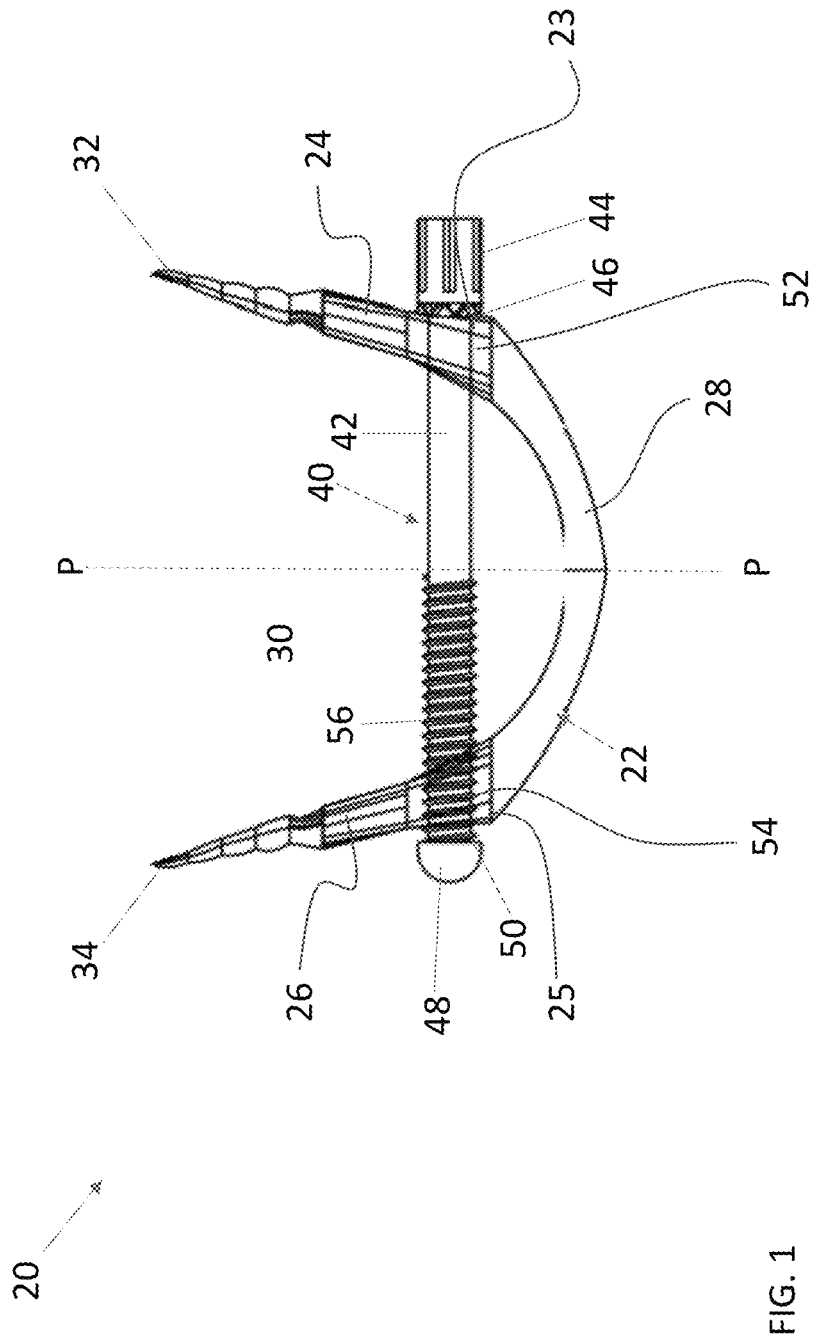
FIG. 1 is a schematic view of a nasal dilator according to an embodiment.

The detailed description explains embodiments of the disclosure, together with advantages and features, by way of example with reference to the drawings.

DETAILED DESCRIPTION

With reference now to the FIGS., examples of a nasal dilator 20 according to various embodiments are illustrated.

As shown, the nasal dilator 20 includes a body 22 having a first leg 24 and a second leg 26. An arcuate connecting member 28 extends between a first end 23, 25 of both the first leg 24 and the second leg 26 to form a body 22 having an approximate U-shape or C-shape. In the illustrated, non-limiting embodiment, the first leg 24, the connecting member 28, and the second leg 26 are integrally formed from a single piece of material. However, it should be understood that embodiments where the body 22 is formed from multiple pieces that are connected, such as welded together for example, are also within the scope of the disclosure.

Figure 2:
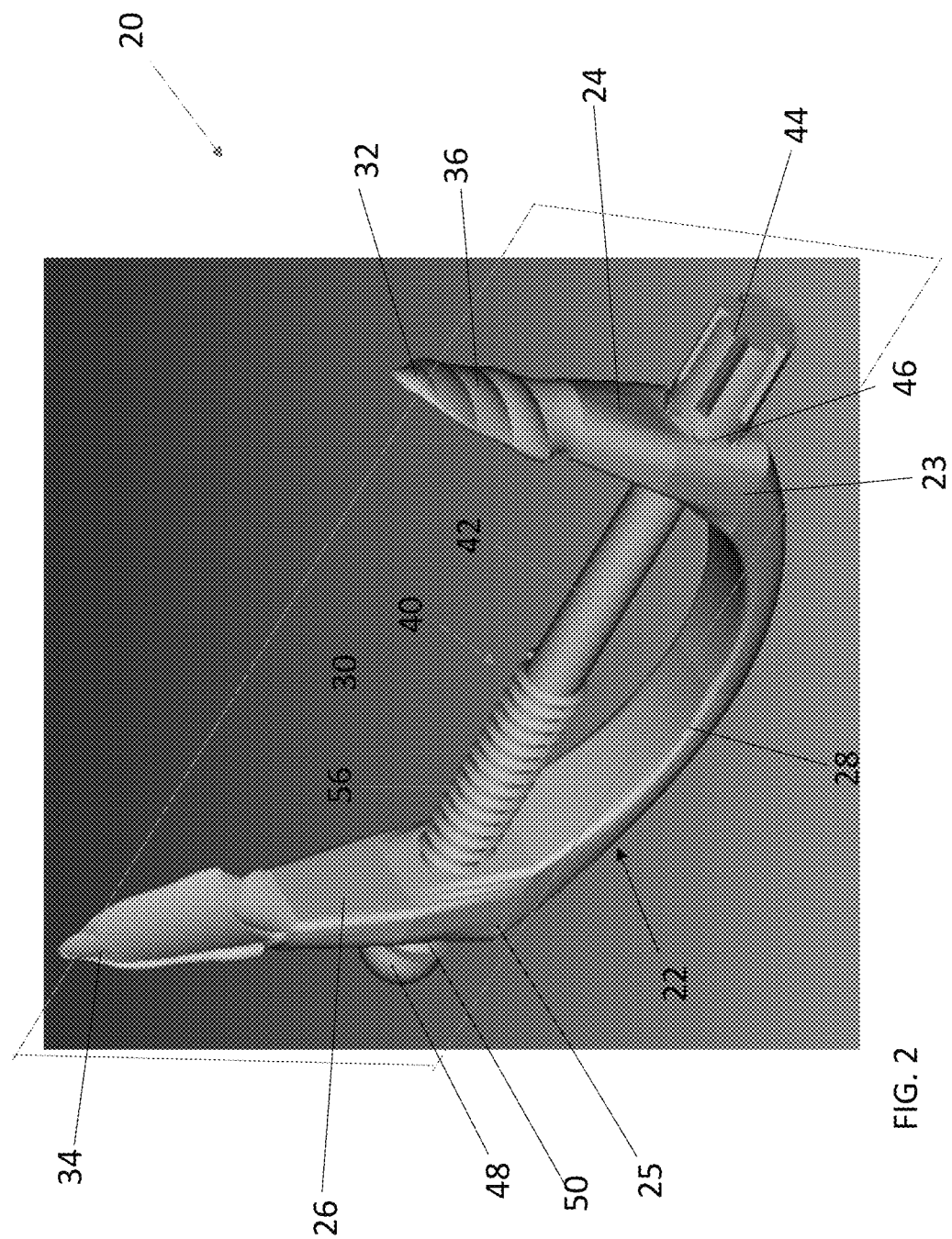
FIG. 2 is a perspective view of a nasal dilator according to an embodiment.

The thickness of the legs 24, 26 may vary over a length of the legs 24, 26. In an embodiment, a thickness of each of the first leg 24 and the second leg 26 (best shown in the plan view of FIGS. 1 and 4) is greatest at the first end, adjacent to the interface with the connecting member 28. From this interface, the thickness of each leg 24, 26 may gradually reduce towards a second distal end 32, 34, respectively, such as for ease of insertion into a nostril cavity or nasal passage. A width of the legs 24, 26, best shown in FIGS. 2 and 3, may similarly taper from the first end of the legs 24, 26 adjacent to the connecting member 28 toward the second distal ends 24, 26 of the legs 24, 26. In other embodiments, the width of the legs 24, 26 may be generally constant over the length of the legs 24, 26. In yet another embodiment, illustrated in FIGS. 3 and 4, the width at the distal end 32, 34 of at least one of the first and second legs 24, 26 is increased width relative to the adjacent portion of the leg 24, 26. Accordingly, the thickness of the legs 24, 26 may taper from the first end toward the distal ends 32, 34 or may be generally constant between the first end and the distal end. In some embodiments, the width at the distal end 32, 34 of the legs 24, 26 is greater than the width at the first end of the leg 24, 26, and therefore forms the widest thickest part of the leg 24, 26. As shown, the distal ends 32, 34 of the legs 24, 26 may have a generally rounded or circular shape, when viewed from the side. However, embodiments where the distal end 32, 34 is another shape, such as rectangular, square, triangular, or polygonal for example, are also within the scope of the disclosure.

Each leg 24, 26 includes a contact region 36 receivable within a nostril cavity. The contact region 36 is configured to directly contact an interior surface of the outer portion of a nostril when the nasal dilator 20 is installed about a user's nose. The outer portion of a nostril is also referred to herein as a "nostril ala." In an embodiment, the contact region 36 is located at the distal end 32, 34 of each leg 24, 26. As shown, the contact region 36 may be defined at an exterior surface of each leg 24, 26. In an embodiment, the contact region 36 is contoured to maximize comfort to a user while also limiting slippage of the nasal dilator 20 relative to the nostril ala at the contact region 36. The contact region 36 may be formed by a pad removably or permanently mounted to a portion of the leg 24, 26, such as in overlapping relationship with the distal end 32, 34 of each leg 24, 26 for example. In other embodiments, the contact region 36 may be formed directly by the leg 24, 26 itself. Accordingly, increasing the width of the distal ends 32, 34 relative to the remainder of the legs 24, 26 may be intended to maximize the size of the contact region 36.

The contact region 36 may include one or more features intended to grip a corresponding interior surface of the nostril ala. In the non-limiting embodiment illustrated in FIGS. 1 and 2, the contact region 36 includes a contoured surface having a plurality of smooth or rounded ridges. In another embodiment, best shown in FIGS. 3 and 4, a plurality of ribs 38 protrude at an angle from the surface of the contact region 36. Although only two ribs 38 are illustrated at each contact region 36, it should be appreciated that embodiments including a single ridge or more than two ribs are also within the scope of the disclosure. The ribs 38 be oriented substantially orthogonally to the longitudinal axis of the leg 24, 26. However, embodiments where the ribs 38 are arranged at another angle relative to the longitudinal axis are also contemplated herein. Further, the ribs 38 may protrude substantially perpendicular from the surface of the contact region 36, or may extend therefrom at another angle. It should be understood that any suitable configuration or contour of the contact region 36 is within the scope of the disclosure.

Figure 3:
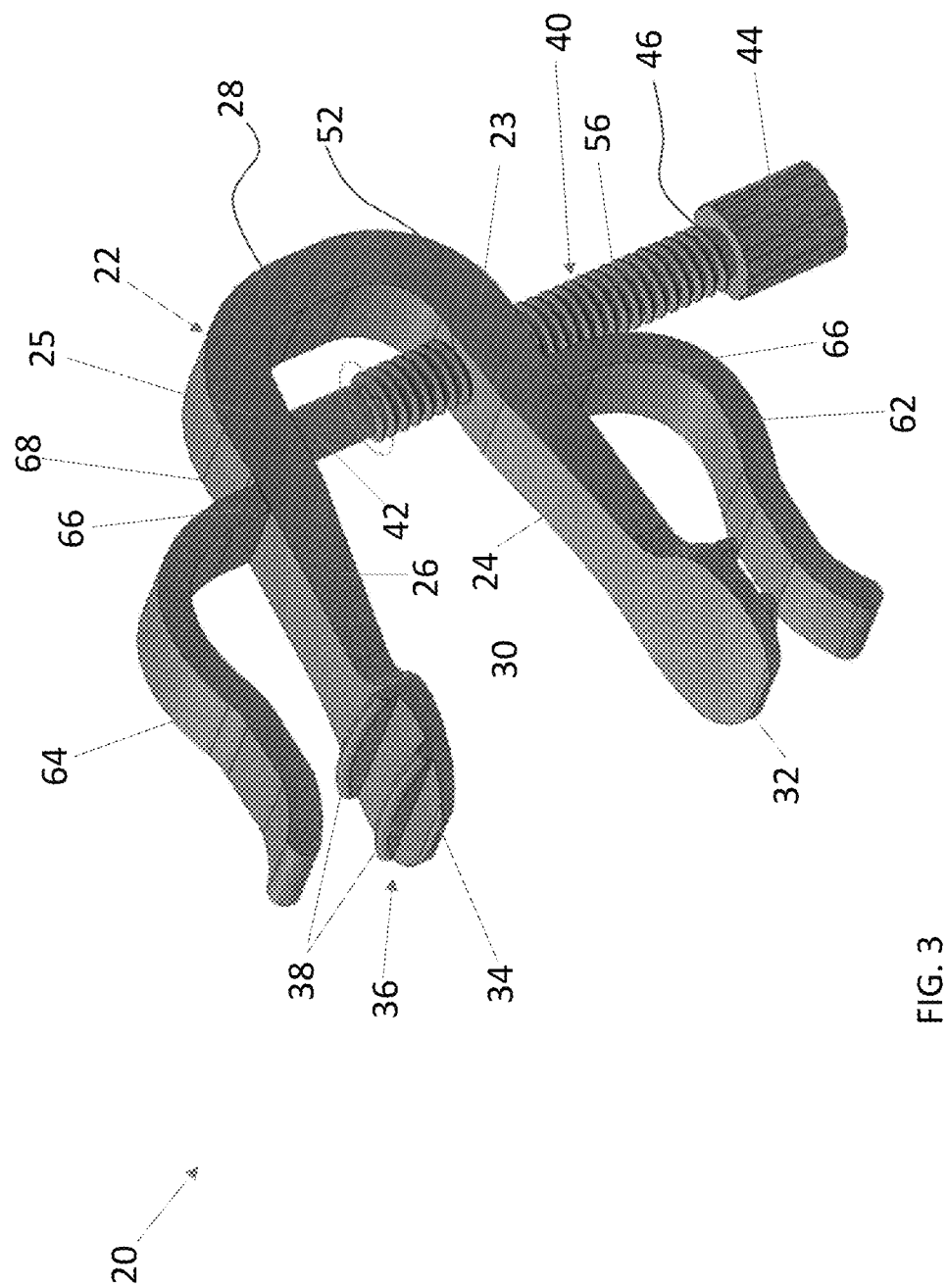
FIG. 3 is a perspective view of a nasal dilator according to another embodiment.
Figure 4:
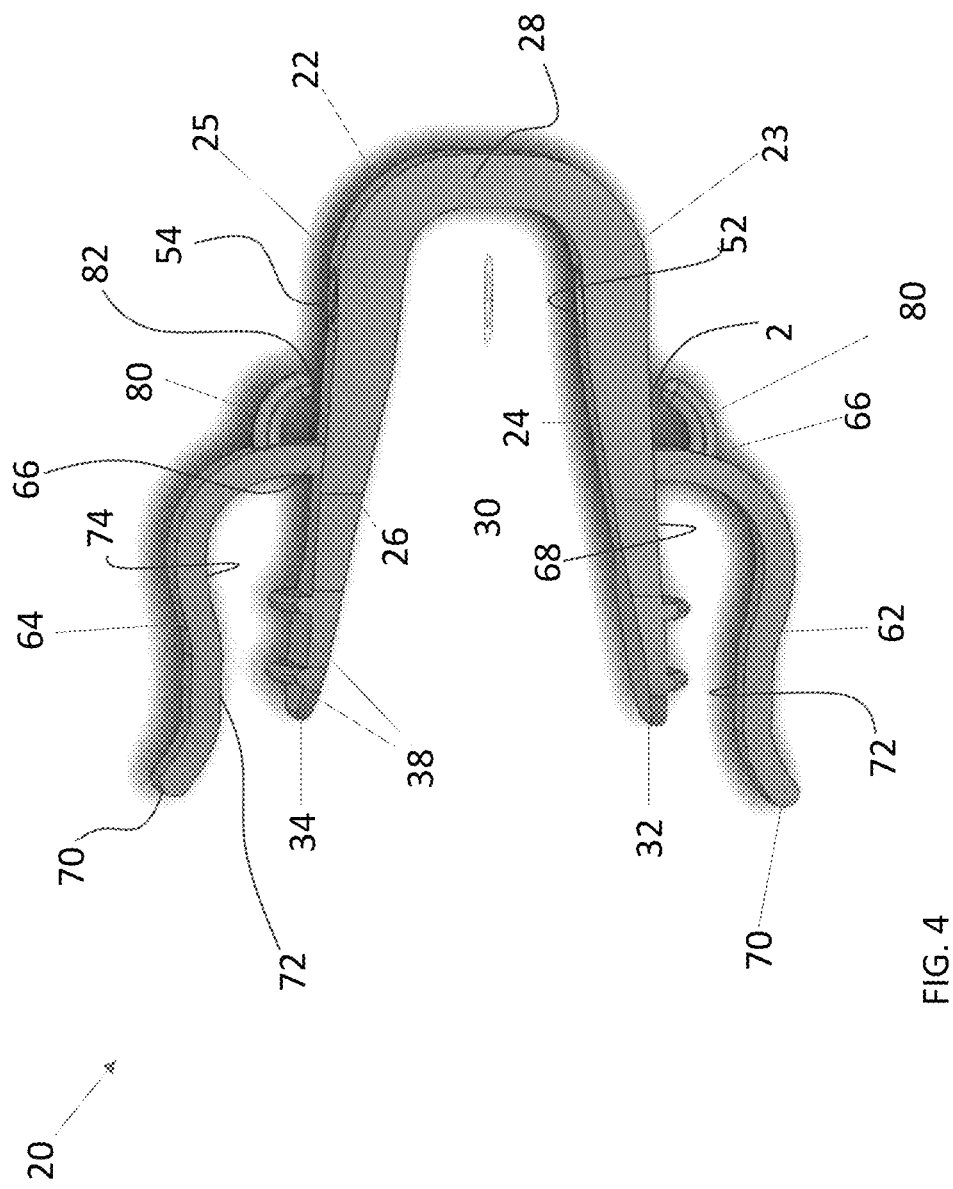
FIG. 4 is a plan view of a nasal dilator according to yet another embodiment.

With continued reference to FIGS. 3 and 4, in an embodiment, the nasal dilator 20 includes at least one support member extending from a portion of the body 22. As shown, the nasal dilator 20 may include a first support member 62 extending from the first leg 24 and a second support member 64 extending from the second leg 26. The support members 62, 64 may be connected to the body 22, or alternatively, may be integrally formed therewith. Each support member 62, 64 may be connected at a first end 66 to an exterior surface 68 of a respective leg 24, 26. Although the first ends 66 of the support members 62, 64 are illustrated as being located near the first end of the legs 24, 26, it should be understood that the support members 62, 64 may be arranged at any location about the body 22 of the nasal dilator 20, such as between the first end and the second distal end 32, 34 of the leg 24, 26, or at the connecting member 28.

A second end 70 of the support members 62, 64 may be substantially aligned with the distal end of the leg 24, 26, as shown in FIG. 3. However, embodiments where the second end 70 of the support members 62, 64 extends beyond the distal end 32, 34 of the leg 24, 26 (see FIG. 4) and embodiments where the second end 70 of the support member 62, 64 is arranged at a position between the first end 23, 25 and the distal end 32, 34 of the leg 24, 26 are also within the scope of the disclosure.

The body of the support member 62, 64 is generally spaced or offset from the exterior surface 68 of the leg 24, 26 by a distance, thereby forming a clearance between the support member 62, 64 and the adjacent leg 24, 26. For example, a first clearance is formed between the first support member 62 and the first leg 24 and a second clearance is formed between the second support member 64 and the second leg 26. When the nasal dilator 20 is installed by a user, the nostril ala is positioned within this clearance between the support member 62, 64 and the leg 24, 26. At least a portion of the support member 62, 64 is configured to contact an exterior surface of the nostril ala when the nasal dilator 20 is installed. The portion of the support member 62, 64 configured to contact an exterior surface of a nostril ala, referred to herein as an external contact region 72, is arranged at an interior or inwardly facing surface 74 of the support member 62, 64. The external contact region 72 may be located at or near a second end 70 of the support member 62, 64 and/or at an intermediate or central portion of the support member 62, 64. In an embodiment, the support member 62, 64 has a generally curved configuration. As a result of the curve, the gap between the support member 62, 64 and the leg 24, 26 varies over the length of the leg 24, 26. The gap between the exterior surface 68 of the leg 24, 26 and the inwardly facing surface 74 of the support member 62, 64 may be smallest at the external contact region 72. By minimizing the gap between the leg 24, 26 and the support member 62, 64 at the external contact region 72, the pressure applied by the external contact region 72 to the nostril ala will stabilize the nasal dilator 20 and prevent unintended movement of the nasal dilator 20 relative to the nose.

In an embodiment, the external contact region 72 is disposed generally opposite at least a portion of the contact region 36. As a result, the external contact region 72 is configured to engage an exterior surface of the nostril ala at the same relative location that the contact region 36 is configured to engage the interior surface of the nostril ala. Accordingly, when installed, the external contact region 72 and the contact region 36 are generally aligned and arranged opposite one another about a nostril ala.

In an embodiment, best shown in FIG. 4, at least one positioning member 80 may extend from the first support member 62 and/or the second support member 64, near a first end thereof. As shown, the positioning member 80 is arranged at an exterior surface of the support members 62, 64 and may have a generally curved or arcuate contour extending toward the first leg 24 and the second leg 26, respectively. A gap 82 may be formed between an end of the positioning members 80 and the exterior surface of the first leg 24 and the second leg 26. Inclusion of the positioning members 80 may be intended to restrict the flexure of the first and second support members 62, 64 relative to the first and second legs 24, 26. For example, if a support member 62, 64 is separated from an adjacent leg 24, 26 by too great a distance, the positioning member 80 will contact the adjacent leg, restricting further outward movement of the support member 62, 64 relative to the leg 24, 26.

The first leg 24 and the second leg 26 may be substantially identical, and the first support member 62 and the second support member 64 if included may be substantially identical, such that the body 22 is generally symmetrical about a central plane P extending through the gap 30 defined between the first leg 24, the connecting member 28, and the second leg 26. The first leg 24 and the second leg 26, and the first support member 62 and the second support member 64 if included, may also be symmetrical about a plane S extending through a center of the first leg 24, the connecting member 28, and the second leg 26. In such embodiments, the nasal dilator 20 may be properly installed within a nose in either a first configuration, or alternatively, in a second configuration, the second configuration being rotated 180 degrees relative to the first configuration. Embodiments where the first leg 24 and the second leg 26 have different configurations, embodiments where an upper surface and a lower surface of a leg 24, 26 have different configurations, and/or embodiments where the first support member 62 and the second support member 64 or the surface thereof have different configurations are also contemplated herein.

The body 22 of the nasal dilator 20 may be formed from any suitable material, including a plastic, metal, or composite material for example. In an embodiment, the body 22 is formed from a resilient or flexible material that allows at least one of the first leg 24 and the second leg 26 to flex or bend for insertion into a nasal cavity. In addition, the support members 62, 64 may be formed from a resilient or flexible material that allows for flexure thereof during installation of the nasal dilator about a nose. The bias of the resilient material will apply a pressure to the outer surface of the nostril ala to facilitate engagement therewith.

In an embodiment, at least a portion of the first leg 24 and the second leg 26 are formed using a non-toxic material having a high flexural strength and the connecting member 28 is formed from a material having a reduced, medium flexural strength. However, embodiments where the legs 24, 26, the support members 62, 64, and/or the connecting member 28 are formed from the same material, such as a high flexural strength material, or alternatively, from a medium flexural strength material are also contemplated herein. Further, in an embodiment, all or a portion of the body 22, such as the distal ends 32, 34 of the legs 24, 26 and/or the second ends 70 of the support members 62, 64, including the contact region 36 and/or external contact region 72 for example, may be coated with a thin layer of soft material, such as with a urethane or silicon for example.

The nasal dilator 20 may be adjustable to accommodate use in different size nasal cavities. More specifically, the distance between the distal end 32 of the first leg 24 and the distal end 34 of the second leg 26 may be varied between a first position and a second position. As shown in the FIGS., the nasal dilator 20 additionally includes an adjustment mechanism 40 operable to adjust the configuration of the body 22. In the illustrated, non-limiting embodiment, the adjustment mechanism 40 is a tension control rod. The tension control rod 40 includes a shaft 42 having a cap or head 44 located at the first end 46 of the shaft 42. In an embodiment, best shown in FIGS. 1 and 2, a nut 48 is located at the second, opposite end 50 of the shaft 42. A first opening 52 may be formed near the first end 23 of the first leg 24, adjacent the interface with the connecting member 28, and a second opening 54 may be formed near the first end 25 of the second leg 26, adjacent the interface with the connecting member 28. The shaft 42 extends through the first opening 52 and the second opening 54 such that the head 44 of the tension control rod 40 is disposed generally adjacent an exterior surface of the first leg 24. In embodiments where the tension control rod 40) includes a nut 48, the nut 48 is located generally adjacent an exterior surface of the second leg 26. In an embodiment, the portion of the body 22 through which the first opening 52 and the second opening 54 are formed is more rigid than the distal ends 32, 34 of the legs 24, 26.

The tension control rod 40 cooperates with the first opening 52 and the second opening 54 to selectively apply a force to the first and second legs 24, 26 to transform the first and second leg 24, 26 between a normal, fully open position (FIG. 1), and a partially closed or retracted position (not shown). In the partially closed or retracted position, a distance between the legs is reduced compared to when the nasal dilator is in a fully open position. However, in all positions, the distal ends 32, 32 of the legs 24, 26 remain separate from one another. In the illustrated, non-limiting embodiment, at least a portion 56 of the shaft 42 of the tension control rod 40 includes a plurality of threads, and at least one of the first opening 52 and the second opening 54 includes a plurality of threads complementary to the threads of the shaft 42. However, embodiments where both the first opening 52 and the second opening 54 are threaded are also within the scope of the disclosure.

A user may apply a rotational force to the tension control rod 40, such as via the head 44 for example, to adjust the configuration of the nasal dilator 20. As the tension control rod 40 is rotated about its axis X in a first direction, the threaded engagement between the second opening 54 and the threaded portion 56 of the shaft 42 applies a force to the second leg 26 of the body 22. Because lateral movement of the shaft 42 relative to the first leg 24 is restricted by the head 44, this rotation causes the second leg 26 to move towards the first leg 24, resulting in a clearance between the nut 48 and the adjacent surface of the leg 26. Because of the resilience or flexure of the material of the leg 26 and the connecting member 28, the leg 26 and/or the connecting member 28 is configured to bend in response to the force, thereby reducing the distance between the distal ends 32, 34 of the legs 24, 26.

When the tension control rod 40 is rotated in a second, opposite direction about the axis X, the resiliency of the material of the legs 24, 26 and connecting member 28, causes the body 22 to bias towards the normal, extended position. The bias of the leg 26 is restricted only by threaded engagement with the shaft 42 and the nut 48. The adjustment mechanism 40) illustrated and described herein is intended as an example only, and it should be understood that other suitable mechanisms for controlling the distance between the distal ends 32, 34 of the legs 24, 26 is within the scope of the disclosure.

To use the nasal dilator 20, an operator may operate the adjustment mechanism 40 until the distal ends of the legs 24, 26 are separated by a distance such that each end 32, 34 is receivable within a corresponding nostril cavity or nasal passage of a user's nose. Once the end 32, 34 of each leg 24, 26 is positioned within a nostril cavity, the adjustment mechanism 40 may be further operated to affix the nasal dilator 20 to the nose. For example, in an embodiment, the distance between the legs 24, 26 may be adjusted to control the pressure applied by the legs 24, 26 to a corresponding portion of the nose, while maintaining a level of comfort experienced by the wearer. In embodiments where the nasal dilator 20 additionally includes at least one support member 62, 64, a user positions the ends 32, 34 of each leg 24, 26 within an interior of the nostril cavity and the support members 62, 64 in contact with an exterior surface of the nostril ala before adjusting the pressure applied by the legs 24, 26 to the interior surface. In such embodiments, the nostril alas should be clamped or sandwiched between the contact regions 36 of the legs 24, 26 and the external contact regions 72 of the support members 62, 64.

When installed relative to the nostril alas and affixed in an operating position, the contact region 36 of each leg 24, 26 is arranged in contact with the tissue arranged at the interior surface of the outer wall of each nostril ala. The nasal dilator 20 does not contact the septum or septal cartilage when properly affixed in an operating position. In an embodiment, the legs 24, 26 are positionable just inside the nostril cavities, in what is referred to as the vestibule of the nose. However, embodiments where the nasal dilator 20 extends beyond the vestibule of the nose are also contemplated herein.

The pressure applied by the legs 24, 26 to the interior surface of the outer wall of each nostril ala is suitable to expand the opening of the nostril (i.e. nasal passage) formed between the septum and the nostril ala. The magnitude of the force is a function of the distance between the distal ends 32, 34 of the legs 24, 26 of the nasal dilator 20. In an embodiment, the force applied by the legs 24, 26, to the interior surface of a nostril ala not only opens the nasal passages, but also, may adjust the geometry of the flow area of each nasal passage. This pressure applied by the legs 24, 26 to the interior surface of the nostril alas opens the nasal passages, thereby increasing the volume of air that can flow into and out of the nose. The nasal dilator 20 may therefore maximize the amount of airflow within the nasal passages relative to existing products. Further, because the nasal dilator 20 is only arranged in direct contact with the interior surface of each nostril ala, and not any other surface within the interior of the nose, such as the particularly sensitive septum for example, the invasiveness of the nasal dilator 20 is minimized, resulting in improved comfortability to the user while the flow through the nasal passages is maximized.

Opening the nasal passages using the nasal dilator 20 as described herein improves the airflow through the nose, thereby reducing the likelihood of the occurrence of a wide variety of sleep related issues including, but not limited to snoring, interrupted sleep, and sleep apnea. Additional benefits of breathing through the nose rather than the mouth include increased oxygen intake and reduced bacteria ingestion.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) is to be construed to cover both the singular and the plural, unless otherwise indicated herein or clearly contradicted by context. The terms "comprising." "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Exemplary embodiments of this disclosure are described herein, including the best mode known to the inventors for carrying out the disclosure. Variations of those embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A nasal dilator comprising:
a first leg and a second leg, the second leg being movable relative to the first leg between a first position and a second position, wherein the second leg is arranged at an angle relative to the first leg in both the first position and the second position;
a first support member extending from the first leg such that a first clearance configured to receive a first nostril ala is formed between the first leg and the first support member;
a second support member extending from the second leg such that a second clearance configured to receive a second nostril ala is formed between the second leg and the second support member; and
an adjustment mechanism including a tension control rod that is extendable through the first and second legs and is rotatable about an axis to move the second leg between the first position and the second position.

2. The nasal dilator of claim 1, wherein the first support member is integrally formed with the first leg and the second support member is integrally formed with the second leg.

3. The nasal dilator of claim 1, wherein a distal end of the first support member and the second support member extends beyond the distal end of the first leg and the second leg, respectively.

4. The nasal dilator of claim 1, wherein a distal end of the first support member and the second support member is aligned with the distal end of the first leg and the second leg, respectively.

5. The nasal dilator of claim 1, further comprises a connecting member coupling the first leg and the second leg.

6. The nasal dilator of claim 5, wherein the first leg, the second leg, and the connecting member are integrally formed.

7. The nasal dilator of claim 1, wherein a first contact region is formed at an exterior surface of the first leg and a second contact region is formed at the exterior surface of the second leg.

8. The nasal dilator of claim 7, wherein at least one of the first contact region and the second contact region includes a contoured surface configured for gripping a nasal surface.

9. The nasal dilator of claim 7, wherein each of the first contact region and the second contact region is formed by a pad mounted to a distal end of the first leg and the second leg, respectively.

10. The nasal dilator of claim 7, wherein a first external contact region is formed at an interior surface of the first support member and a second external contact region is formed at the interior surface of the second support member.

11. The nasal dilator of claim 10, wherein the first contact region is aligned with the first external contact region and the second contact region is aligned with the second external contact region.

12. The nasal dilator of claim 10, wherein the first support member and the second support member have a curved configuration such that the first clearance varies over a length of the first leg and the second clearance varies over the length of the second leg.

13. The nasal dilator of claim 12, wherein the first clearance is smallest between the first contact region and the first external contact region and the second clearance is smallest between the second contact region and the second external contact region.

14. The nasal dilator of claim 1, wherein the first support member and the second support member are formed from a resilient material.

15. The nasal dilator of claim 1, wherein lateral movement of the tension control rod is restricted relative to at least one of the first leg and the second leg.

16. The nasal dilator of claim 1, wherein the tension control rod is threadably coupled to at least one of the first leg and the second leg.

* * * * *